US011998376B2

(12) United States Patent
Zeidler et al.

(10) Patent No.: US 11,998,376 B2
(45) Date of Patent: Jun. 4, 2024

(54) METHOD FOR GENERATING TRAINING DATA FOR TRAINING AN ALGORITHM FOR ESTIMATING POSITIONING VARIANCES IN AN IMAGING APPARATUS OF AN X-RAY IMAGING SYSTEM

(71) Applicant: Siemens Healthcare GmbH, Erlangen (DE)

(72) Inventors: Josef Zeidler, Marktredwitz (DE); Alexander Krämer, Irchenrieth (DE); Gerhard Wurzer, Mantel (DE); Berthold Baumann, Kastl (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/212,864

(22) Filed: Jun. 22, 2023

(65) Prior Publication Data

US 2024/0000409 A1 Jan. 4, 2024

(30) Foreign Application Priority Data

Jun. 29, 2022 (DE) ...................... 10 2022 206 561.1

(51) Int. Cl.
*A61B 6/00* (2006.01)
*G06T 7/00* (2017.01)
(Continued)

(52) U.S. Cl.
CPC .......... *A61B 6/4458* (2013.01); *A61B 6/4441* (2013.01); *G06T 7/0012* (2013.01);
(Continued)

(58) Field of Classification Search
CPC ..... A61B 6/405; A61B 6/4441; A61B 6/4458; A61B 6/4464; A61B 6/4482; A61B 6/547;
(Continued)

(56) References Cited

U.S. PATENT DOCUMENTS

2020/0286264 A1* 9/2020 Kaethner .............. G06T 11/005
2022/0051401 A1 2/2022 Lenich
(Continued)

FOREIGN PATENT DOCUMENTS

CN 111260748 A 6/2020
CN 114140374 A 3/2022
(Continued)

*Primary Examiner* — Dani Fox
(74) *Attorney, Agent, or Firm* — Lempia Summerfield Katz LLC

(57) ABSTRACT

A computer-implemented method for generating training data for training an algorithm for estimating positioning variances in an imaging apparatus of an x-ray imaging system is provided. The method includes predetermining target positioning data for the imaging apparatus and calculating faulty positioning data, wherein the faulty positioning data deviates from the target positioning data by at least one predetermined positioning variance. An imaging method is simulated, in order to generate two or more simulated x-ray recordings, wherein a positioning of the imaging apparatus is simulated in accordance with the faulty positioning data. An annotated training data record is generated and stored, wherein the training data record contains two or more simulated x-ray recordings and at least one positioning variance as an annotation of the two or more simulated x-ray recordings.

16 Claims, 2 Drawing Sheets

(51) Int. Cl.
*G16H 50/20* (2018.01)
*A61B 6/40* (2024.01)

(52) U.S. Cl.
CPC .............. *G16H 50/20* (2018.01); *A61B 6/405* (2013.01); *G06T 2207/20081* (2013.01)

(58) Field of Classification Search
CPC ....... A61B 6/584; A61B 90/00; G06T 11/003; G06T 2207/20081; G06T 7/00; G06T 7/0012
See application file for complete search history.

(56) References Cited

U.S. PATENT DOCUMENTS

| | | |
|---|---|---|
| 2022/0058437 A1 | 2/2022 | Soni |
| 2022/0193453 A1 | 6/2022 | Miyazaki |

FOREIGN PATENT DOCUMENTS

| | | |
|---|---|---|
| CN | 114155402 A | 3/2022 |
| EP | 3706081 A1 | 9/2020 |

\* cited by examiner

METHOD FOR GENERATING TRAINING DATA FOR TRAINING AN ALGORITHM FOR ESTIMATING POSITIONING VARIANCES IN AN IMAGING APPARATUS OF AN X-RAY IMAGING SYSTEM

The present patent document claims the benefit of German Patent Application No. 10 2022 206 561.1, filed Jun. 29, 2022, which is hereby incorporated by reference in its entirety.

TECHNICAL FIELD

The present disclosure relates to a computer-implemented method for generating training data for training an algorithm for estimating positioning variances in an imaging apparatus of an x-ray imaging system. The disclosure further relates to a corresponding computer-implemented method for training an algorithm for estimating positioning variances in an imaging apparatus of an x-ray imaging system, a method for x-ray imaging, a data processing apparatus, and a computer program product.

BACKGROUND

With the generation of x-ray image recordings, the achievable resolution of the diagnostic data may be reduced and/or interfering artifacts may result, if variances in the positioning of an imaging apparatus of an x-ray imaging system, in other words the imaging components such as the x-ray source or the x-ray emitter and the x-ray detector, develop with respect to the object to be mapped.

This is particularly relevant when a number of x-ray recordings, in particular two-dimensional x-ray recordings, are created and further processed, (e.g., during the subtraction image calculation), with which images are generated with and without administering contrast agent and are offset against one another. Here a variance in the positioning in the case of individual recordings may result in artifacts and blurring or a reduced resolution. Also, with methods for three-dimensional image reconstruction, in which a plurality of two-dimensional x-ray recordings are generated at different positions in the imaging apparatus with respect to the object to be mapped and are then combined with one another for a three-dimensional reconstruction, blurring and interfering artifacts may develop if variances in the actual trajectory of the imaging apparatus from a target trajectory exist.

The variances may trace back to tolerances or clearance of the kinematic axes of the x-ray imaging system or to oscillations after reaching a position for instance or also to movements of the object etc.

To counteract this problem, stands with very high rigidity and drive components or guide systems with very low tolerances are used for correspondingly sensitive x-ray imaging methods in order to enable high positioning accuracy. This results in the stands being very complex and expensive to manufacture and having a very high weight.

If such stands are not to be used, there is therefore the need to be able to estimate developing positioning variances as accurately as possible in order to be able to take these into account during the image reconstruction.

SUMMARY AND DESCRIPTION

One object of the present disclosure is to enable an estimation of positioning variances in an imaging apparatus of an x-ray imaging system with increased accuracy.

The scope of the present disclosure is defined solely by the appended claims and is not affected to any degree by the statements within this summary. The present embodiments may obviate one or more of the drawbacks or limitations in the related art.

The disclosure is based on the idea of providing training data, with which an algorithm may be trained for estimating positioning variances in an imaging apparatus of an x-ray imaging system. To this end, an annotated training data record is generated, which contains two or more simulated x-ray recordings, which are simulated in accordance with faulty positioning data, which deviates from target positioning data by a predetermined positioning variance. The positioning variance is used as an annotation of the simulated x-ray recordings. The training data thus generated may be used to train a corresponding algorithm and the trained algorithm may be used to estimate positioning variances while actually generating x-ray recordings.

In accordance with one aspect, a computer-implemented method is specified for training an algorithm for estimating positioning variances in an imaging apparatus of an x-ray imaging system. In this regard, target positioning data is predetermined for the imaging apparatus and faulty positioning data is calculated as a function of the target positioning data, the faulty positioning data deviating from the target positioning data by at least one predetermined positioning variance. An imaging method is simulated, in order to generate two or more simulated x-ray recordings, (e.g., two-dimensional x-ray recordings), wherein a positioning of the imaging apparatus is simulated in accordance with the faulty positioning data. An annotated training data record is generated and stored. The annotated training data record contains the two or more simulated x-ray recordings and the at least one positioning variance as an annotation of the two or more simulated x-ray recordings.

Unless indicated otherwise, all acts of the computer-implemented method may be carried out by at least one computing unit, which may also be referred to as data processing apparatus. In particular, the data processing apparatus includes at least one processing circuit, which is configured to carry out the acts of the computer-implemented method. To this end, a computer program may be stored in the data processing apparatus, the computer program including instructions that trigger the data processing apparatus to execute the computer-implemented method, upon execution by the data processing apparatus, in particular the at least one processing circuit.

The imaging apparatus contains in particular an x-ray detector or x-ray sensor and an x-ray source or an x-ray emitter. For instance, the x-ray source is fixed with respect to the x-ray detector so that with a change in positioning of the imaging apparatus, the position and orientation of the x-ray detector does not change with respect to the x-ray source. For instance, the imaging apparatus may be fastened to a stand, which may also be referred to as robot stand, and may move and thus position the imaging apparatus relative to the object to be mapped according to one or more degrees of translational and/or rotational freedom, also referred to as kinematic axes, in particular translation axes or axes of rotation. The stand may be a mobile stand or a stand which may be mounted on a wall or a ceiling of a building. For instance, a C-arm may be a stand.

The x-ray imaging apparatus may also contain a patient couch or a patient table or suchlike, on which a patient or another object to be mapped may be placed.

The x-ray imaging apparatus may include a drive apparatus in order to control the different kinematic axes of the stand and as a result to move and position the imaging apparatus accordingly in a reference coordinate system. The reference coordinate system may be fixedly connected to the patient couch or the patient table for instance or to a surface upon which the stand is located. In particular, a position or positioning of the imaging apparatus, unless something else is not expressly mentioned, may refer to a position or positioning in the reference coordinate system, e.g., with respect to the patient couch.

The term "positioning" may be summarized here and below in such a way that the term not only relates to a position in the narrower sense, but instead also to an orientation or a combination of the position and orientation, in other words a pose or location, of the imaging apparatus in the reference coordinate system. A positioning may therefore refer to a setting of a position and/or orientation. Positioning data may contain positions of the individual kinematic axes of the stand, for instance. In various embodiments, the x-ray imaging system may have a further drive apparatus for the patient couch. A position and/or orientation of the patient couch may therefore be influenced independently of the positioning of the stand. The positioning of the imaging apparatus may also be influenced in this way.

By specifying the corresponding axes positions of all kinematic axes of the stand and if available the kinematic axes of the patient couch, a positioning of the imaging apparatus may be uniquely determined, wherein this does not exclude different combinations of the axes positions being able to result in one and the same positioning of the imaging apparatus.

For instance, the target positioning data for each kinematic axis of the x-ray imaging system may contain a corresponding target value for the corresponding axis position. These target values may be given for two or more time instants, wherein each of the two or more simulated x-ray recordings is assigned to one of the two or more time instants. With a real x-ray imaging, a corresponding x-ray recording would be recorded at each of the two or more time instants. If the target values for different time instants differ from one another, this may refer to a trajectory in a (e.g., multi-dimensional) space, which is covered by the axis positions of the individual axes. Alternatively, the target positioning data may however also contain the position and/or orientation of the imaging apparatus in the reference coordinate system directly.

Accordingly, the at least one positioning variance contains for instance a variance relating to the position of one or more of the axes of the x-ray imaging system from the respective target value or the respective target position for one or more time instants, for which the target positioning data is given. Alternatively, by the at least one predetermined positioning variance, a variance in the orientation and/or position of the imaging apparatus may also be specified directly in the reference coordinate system.

The fact that the target positioning data is predetermined may mean that the target positioning data is stored in computer-readable form on a data medium of the x-ray imaging system. The at least one positioning variance may likewise be stored in advance or in accordance with predetermined rules when the method is implemented. The predetermined variance may be determined for instance at random or statistically or according to a predetermined statistical distribution so that the actual values of the positioning variance do not necessarily have to be known in advance, provided the rule for determining the at least one positioning variance is known and predetermined.

The target positioning data therefore defines a target positioning of the imaging apparatus for the two or more time instances in each case. Depending on the application case, the target positionings may differ from one another with respect to different time instants, for instance if the target positioning data specifies a trajectory for three-dimensional image reconstruction, or also not, for instance if different x-ray recordings are to be generated at one and the same target positioning, for instance for subtraction angiography.

Similarly, the faulty positioning data define a positioning of the imaging apparatus for each of the two or more time instants. The positionings defined by the faulty positioning data may correspond in part to the target positionings. There is, however, a variance with respect to the corresponding target positioning of the same time instant, which is fixed by the at least one predetermined positioning variance, at least for one of the positionings, which are defined by the faulty positioning data. Alternatively, or additionally, the variance may also be given by temporal variances in the two or more time instants from one another.

To simulate the imaging method, a simulated x-ray recording is generated for each of the two or more time instants, so that the two or more simulated x-ray recordings result. To this end, it is assumed for each of the two or more time instants that the imaging apparatus is positioned in accordance with the corresponding positioning defined by the faulty positioning data with respect to a test object, in particular a virtual test object. The virtual test object is defined here in particular by a spatial distribution of an attenuation coefficient, in particular an x-ray attenuation coefficient.

Furthermore, an x-ray dose, an x-ray beam form, a dose curve, or a curve of the beam form may be predetermined. Furthermore, further properties of an optics, in particular a beam guiding optics or suchlike, may also be predetermined. On the basis of this data and assumptions, it is then possible to simulate or calculate how an x-ray recording of the test object would look under the given conditions, in particular with the corresponding positioning. In this way, the two or more simulated x-ray recordings are therefore generated. Furthermore, a known beam-optical model or x-ray mapping model may form the basis of the simulation. The simulation may therefore contain a co-simulation of mechanics, drive technology, and x-ray imaging.

The two or more simulated x-ray recordings combined with the corresponding faulty positioning data used for their generation may therefore be used as an annotated training data record for training an algorithm that may be trained by machine learning. The described acts for generating the annotated training data record may be repeated multiple times for instance, wherein the at least one predetermined positioning variance is changed for each repetition. A plurality of annotated training data records may be generated in this way and may then be used to correspondingly train the algorithm.

Alternatively, or additionally, to varying the at least one positioning variance with the different repetitions, the target positioning data may also be varied with different repetitions.

The algorithm for estimating positioning variances may be implemented in a variety of ways. This involves an algorithm, which may be trained on the basis of the training data or the annotated training data record in accordance with a per se known machine learning method which operates on the basis of annotated training data. To this end, a positioning variance may be predicted by the algorithm based on the simulated x-ray recordings and the prediction may be offset against the annotation of the training data record, in other words the predetermined positioning variance, in order to calculate or evaluate an error function or cost function or suchlike. The algorithm may then be adjusted and thus trained as a function thereof.

For instance, the algorithm contains one or more artificial neural networks, for instance "Convolutional Neural Networks" (CNN). Neural networks, in particular CNNs, are very well suited to predicting inherent parameters or features of two-dimensional mappings, in other words also x-ray recordings and are very efficient. It is also possible to use recurrent neural networks, RNN, for instance LSTMs ("Long Short Term Memory") in order also to be able to capitalize on a temporal relationship in the two or more x-ray recordings in the training data record. The architecture of the algorithm is not the subject matter of the present disclosure, however.

By the repeated application of the computer-implemented method for generating training data, one possibility is provided of training positioning variances, in particular inaccuracies in the positioning or path guidance of the imaging apparatus.

As a result, such positioning variances may therefore consequently be taken into consideration in the generation of x-ray recordings, in particular two-dimensional x-ray recordings, and these x-ray recordings may be corrected. These corrected x-ray recordings may be offset, for instance for three-dimensional image reconstruction or for subtraction imaging, so that artifacts or blurring or reduced resolution may be reduced in the end results. Alternatively, or additionally, the variances may also be taken into consideration directly during the image reconstruction.

As a result, it is possible to reduce the requirements on the positioning accuracy and path accuracy of the x-ray imaging system, in particular the stand. As a result, in particular stands with a lower weight or lower rigidity may be used, without significantly impairing the quality of the end results of the x-ray imaging. Alternatively, with the use of highly rigid and heavy stands, artifacts and blurring may be further reduced in the end results.

In accordance with at least one embodiment of the computer-implemented method, the target positioning data establishes a target trajectory for the imaging apparatus and the faulty positioning data establishes a faulty trajectory for the imaging apparatus.

In other words, the target positionings for the two or more time instants differ in the target positioning data. The simulation of the positioning of the imaging apparatus therefore corresponds to a simulation of a movement along the faulty trajectory. The trajectory may be given here in particular in the space of all kinematic axes of the x-ray imaging system or in the reference coordinate system.

Such embodiments are in particular advantageous in order to estimate positioning variances in three-dimensional image reconstructions or suchlike.

For instance, the target trajectory for a target positioning of the imaging apparatus establishes a target time instant and the faulty trajectory establishes a faulty time instant for the target positioning of the imaging apparatus, the faulty time instant differing from the target time instant corresponding to the at least one positioning variance.

In other words, the positioning variance cannot only be defined as a variance of the target positioning, but, as in corresponding embodiments, as variance of the corresponding time instants from one another. As a result, situations may be taken into account in which, on account of tolerances or interferences or suchlike, the movement of the imaging apparatus from one positioning to the next takes place more or less quickly. Such positioning variances may also be taken into account accordingly by the training data.

In accordance with at least one embodiment, a first target positioning of the imaging apparatus differs for a first simulated x-ray recording of the two or more simulated x-ray recordings according to the target positioning data from a second target positioning of the imaging apparatus for a second simulated x-ray recording of the two or more simulated x-ray recordings according to the target positioning data. The difference is given in particular by a target relative pose. A first faulty positioning of the imaging apparatus for the first simulated x-ray recording in accordance with the faulty positioning data differs from a second faulty positioning of the imaging apparatus for the second simulated x-ray recording from the faulty positioning data according to a faulty relative pose, which deviates from the target relative pose.

A target pose of the imaging apparatus is defined in each case by the first target positioning and the second target positioning. The target relative pose is given by the target pose according to the first target positioning with respect to the target pose in accordance with the second target positioning or vice versa.

The same applies accordingly to the faulty relative pose. The faulty relative pose deviates here from the target relative pose in particular according to the at least one predetermined positioning variance.

In such embodiments, a difference between the target positions of the imaging apparatus for generating the first and the second x-ray recording is therefore unequal to the corresponding difference in the positions in accordance with the faulty positioning data, for instance. Alternatively, or additionally, a corresponding inequality may be given in the orientations.

Such variances may be caused by tolerances in the individual axes, also referred to as axle clearance, of the x-ray imaging system or oscillations in the stand. Such positioning variances are also relevant in particular for 3D reconstructions.

According to at least one embodiment, a third target positioning of the imaging apparatus for a third of the two or more simulated x-ray recordings in accordance with the target positioning data matches with a fourth target position of the imaging apparatus for a fourth of the two or more simulated x-ray recordings according to the target positioning data. A third faulty positioning of the imaging apparatus for the third simulated x-ray recording in accordance with the faulty positioning data deviates from a fourth faulty positioning of the imaging apparatus for the fourth simulated x-ray recording in accordance with the faulty positioning data.

In other words, the positionings for the third x-ray recording and the fourth x-ray recording are to be identical, for instance in order to offset against one another, for instance within the scope of a subtraction reconstruction or subtraction evaluation. However, the faulty positioning data instead indicates a variance.

Such positioning variances may also be caused by tolerances in the axes or oscillations of the stand.

In accordance with at least one embodiment, the at least one positioning variance is determined for the positioning of the imaging apparatus in accordance with a predetermined model, for instance a predetermined statistical model.

In this way, realistic positioning variances based on distributions to be expected within predetermined tolerance ranges or suchlike may form the basis of the generation of the training data, as a result of which the training of the algorithm may be improved.

For instance, the positioning of the imaging apparatus is fixed by respective axis positions of the kinematic axes of the x-ray imaging system. The model contains a statistical position distribution according to a predetermined axle clearance for one of the kinematic axes. The at least one positioning variance is determined as a function of the statistical position distribution.

Accordingly, the at least one positioning variance may be determined at random in accordance with the position distribution in order thus to realistically reproduce or take into account the axle clearance of the kinematic axes of the x-ray imaging system.

The positioning distribution may be given for instance by a Gaussian distribution with a predetermined width dependent upon the respective axle clearance. As a result, it is possible to simulate a simple and thus realistic estimation of developing positioning variances.

In accordance with at least one embodiment, the calculation of the faulty positioning data, the simulation of the imaging method and the generation and storage of the annotated training data record are repeated multiple times, wherein with each repetition, the at least one positioning variance is determined again as a function of the statistical position distribution.

In this way, the generated training data therefore contains a plurality of annotated training data records according to different statistically relevant positioning variances.

In accordance with at least one embodiment, the model for a second axis of the two or more kinematic axes contains a reverberation characteristic and the at least one positioning variance is determined at least in part in accordance with the reverberation characteristic.

Here the reverberation characteristic may describe in particular how, after changing the positioning to a target positioning, the actual positioning oscillates about the target positioning. In particular, an oscillation amplitude or a damping characteristic of the oscillation may be included in the reverberation characteristic. In this way, positioning variances may be estimated realistically.

In accordance with at least one embodiment, target dose data is predetermined, and faulty dose data is calculated as a function of the target dose data, the faulty dose data deviating from the target dose data by at least one dose variance. When the imaging method is simulated, the emission of x-ray radiation is simulated in accordance with the faulty dose data. The annotated training data record contains the at least one dose variance as a further annotation of the two or more simulated x-ray recordings.

In this way, by the training data, it is not only the positioning variances, but moreover instead also dose fluctuations in the x-ray radiation dose, which are used when the x-ray recordings are generated, which are taken into account and the algorithm is trained accordingly in order to predict the positioning variances and the dose fluctuations and are used accordingly after training.

By combining the prediction both of the dose fluctuations and also of the positioning variances, artifacts and blurring may be compensated for more effectively or are avoided.

In accordance with at least one embodiment, the at least one dose variance is determined according to a predetermined statistical dose distribution.

The dose distribution therefore corresponds to a probability distribution for the dose by a predetermined dose target value. The distribution may likewise be a Gaussian distribution of a predetermined width, for instance.

The dose distribution may also be different for different time instants and accordingly for different of the two or more x-ray recordings.

As described with respect to the repetition by varying the at least one positioning variance, the corresponding acts may also be repeated by varying the at least one dose variance, in order thus to generate a plurality of corresponding training data records with different dose variances.

In accordance with a further aspect, a computer-implemented method is specified for training an algorithm for estimating positioning variances in an imaging apparatus of an x-ray imaging system. Here, a computer-implemented method is carried out in order to generate training data. At least one positioning variance is predicted by applying the algorithm to the two or more simulated x-ray recordings. The algorithm is adjusted as a function of the at least one predicted positioning variance and the at least one positioning variance of the annotated training data record.

For instance, a predetermined cost function may be evaluated as a function of the at least one predicted positioning variance and the at least one positioning variance, in particular of a difference in the respective variables. The algorithm may then be adjusted as a function of a result of the evaluation of the cost function, in order to train the same.

In the case of one or more neural networks, a back propagation algorithm may be used for training purposes, for instance. The corresponding acts may be repeated for different annotated training data records, in order to iteratively improve the training of the algorithm or to iteratively improve the training state, until a predetermined abort criterion is reached, and the algorithm is sufficiently trained accordingly.

In accordance with a further aspect, a method for x-ray imaging is specified. Here two or more x-ray recordings, in particular two-dimensional x-ray recordings, of an object to be mapped are generated by an x-ray imaging system, wherein an imaging apparatus is positioned in accordance with a predetermined target positioning data, in particular by the drive apparatus and/or the further drive apparatus of the x-ray imaging system. At least one positioning variance is estimated by applying an algorithm to the two or more x-ray recordings generated, wherein the algorithm is or has been trained in accordance with a computer-implemented method for training an algorithm for estimating positioning variances of an imaging apparatus of an x-ray imaging system. The two or more generated x-ray recordings are corrected as a function of the at least one estimated positioning variance.

The corrected x-ray recordings may then be used advantageously for reconstruction, for instance for three-dimensional x-ray image reconstruction or for subtraction angiography, wherein artifacts and/or blurring are reduced or avoided in the result of the reconstruction.

The implementation of the computer-implemented method for training the algorithm may also be part of the method for x-ray imaging.

In accordance with at least one embodiment of the method for x-ray imaging, a three-dimensional reconstruction of the object to be mapped is generated on the basis of the corrected two or more x-ray recordings and/or at least one subtraction angiography mapping of the object to be mapped is generated on the basis of the corrected two or more x-ray recordings.

For application cases or application situations, which may result with the method, and which are not described explicitly here, provision may be made in accordance with the method for an error message and/or a request to input a user feedback to be output and/or for a standard setting and/or a predetermined initial state to be set.

In accordance with a further aspect, a data processing apparatus with at least one processing switching circuit is specified, which is adjusted to execute a computer-implemented method for generating training data and/or a computer-implemented method for training an algorithm. The data processing apparatus corresponds for instance to one or more computing units.

A computing unit may refer to a data processing device that contains a processing switching circuit. The computing unit may therefore process, in particular, data for carrying out computing operations. This also includes, where relevant, operations to carry out indicated access operations to a data structure, for example, a look-up table (LUT).

The computing unit may contain in particular one or more computers, one or more microcontrollers, and/or one or more integrated switching circuits, for instance one or more application-specific integrated circuits (ASIC), one or more field-programmable gate arrays (FPGA), and/or one or more one chip systems or "system on a chip" (SoC). The computing unit may also contain one or more processors, for instance one or more microprocessors, one or more central processor units (CPUs), one or more graphics processing units (GPUs), and/or one or more signal processors, in particular one or more digital signal processors (DSPs). The computing unit may also include a physical or a virtual group of computers or other of the units.

In different exemplary embodiments, the computing unit contains one or more hardware and/or software interfaces and/or one or more storage units.

In accordance with a further aspect, an x-ray imaging system is specified that contains a data processing apparatus. The x-ray imaging system has an imaging apparatus, a stand, and a drive apparatus, as described above.

A method for x-ray imaging may therefore be carried out by the x-ray imaging system.

In accordance with a further aspect, a computer program is specified with commands. If the commands are executed by a data processing apparatus, in particular a data processing apparatus, the commands trigger the data processing apparatus to execute a computer-implemented method for generating training data and/or a computer implemented method for training an algorithm for estimating positioning variances.

In accordance with a further aspect, a computer-readable storage medium is specified, which stores a computer program as disclosed herein.

The computer program and the computer-readable storage medium may be understood to be a respective computer program product with the commands.

DETAILED DESCRIPTION

Figure 1:
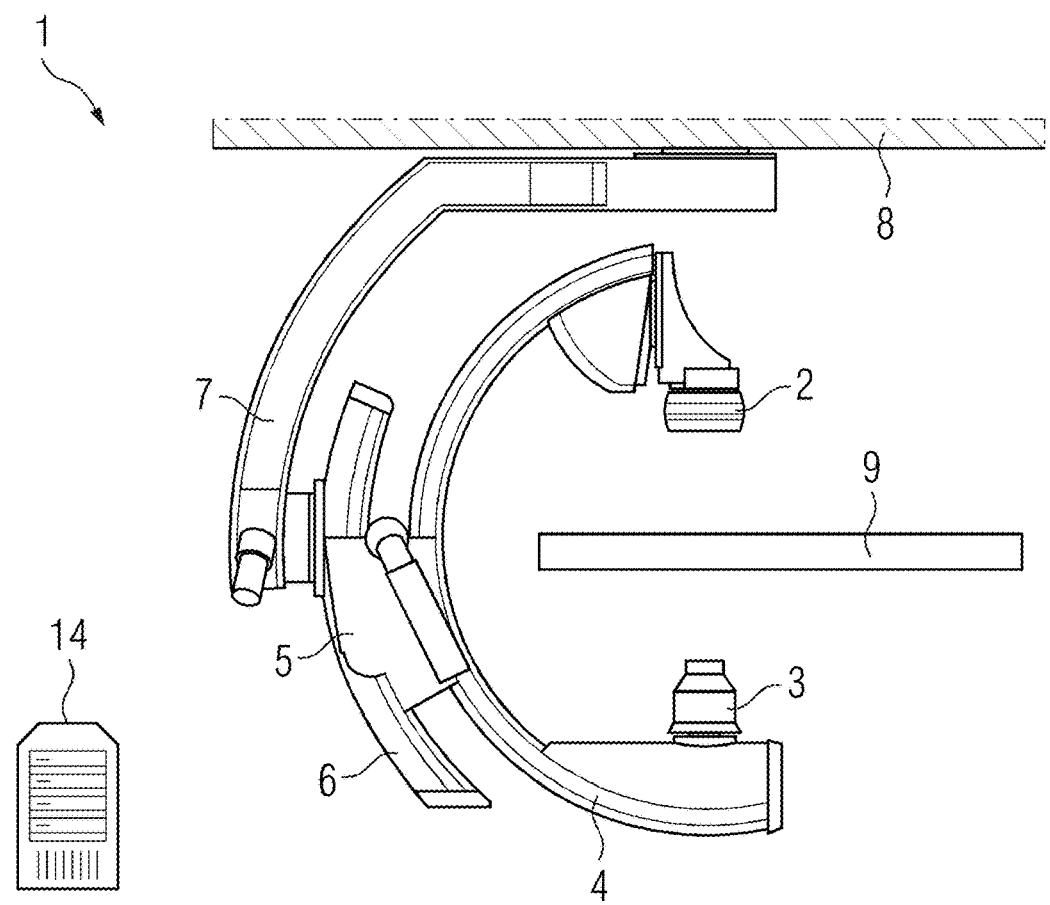
FIG. 1 depicts a schematic representation of an exemplary embodiment of an x-ray imaging system and a data processing apparatus and a schematic flow chart of an exemplary embodiment of a method for training an algorithm for estimating positioning variances in an imaging apparatus of the x-ray imaging system.
Figure 1:
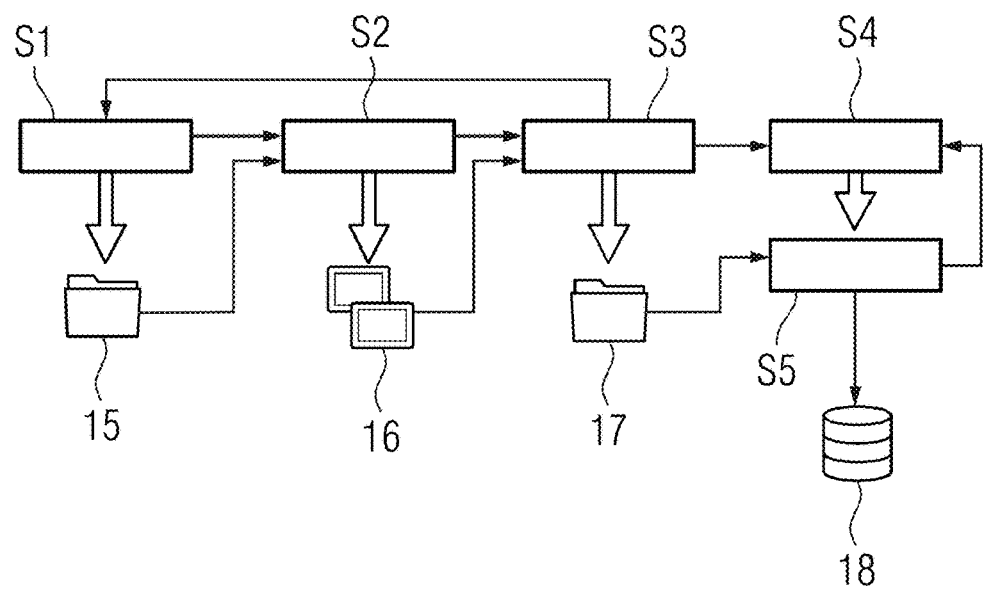

FIG. 1 shows a schematic representation of an x-ray imaging system 1 and a data processing apparatus 14.

By the data processing apparatus 14, an exemplary embodiment of a computer-implemented method is carried out for training an algorithm 18 for estimating positioning variances in an imaging apparatus, which has for instance an x-ray source 3 and an x-ray detector 2 of the x-ray imaging system 1. A schematic flow chart with acts S1 to S5 of such a method is likewise shown in FIG. 1, wherein the acts S1 to S3 represent an exemplary embodiment of a computer-implemented method for generating training data for training the algorithm 18.

The x-ray imaging system 1 is shown by way of example in FIG. 1 as a ceiling-mounted C-arm device with a patient couch 9. However, the disclosure is not restricted to such embodiments of the x-ray imaging system 1.

A stand of the x-ray imaging system 1 has for instance a main arm 7, which may be fastened to a ceiling 8, in some embodiments in a rotatable manner. The main arm 7 and thus the entire stand may then rotate about an axis at right angles to the ceiling 8, for instance. An intermediate arm 6 is fastened to the main arm 7 by way of a rotatable connection 15. A C-arm 4 is fastened to the intermediate arm 6 by way of a slide 5. The x-ray source 3 and the x-ray detector 2 are fastened to the C-arm 4.

When the main arm 7 rotates, the complete stand rotates therewith, in particular the C-arm 4. The C-arm 4 may be rotated together with the intermediate arm 6 about a further axis, wherein the main arm 7 remains fixed. The C-arm 4 is fastened to the intermediate arm 6 by way of the slide 5 such that it may slide along the intermediate arm 6 independently of the rotational movement of the C-arm 4 and the intermediate arm 6, so that a rotation about a further axis results, which is also referred to as an orbital rotational movement of the C-arm 4. This orbital rotational movement of the C-arm 4 may be carried out independently of a movement of the intermediate arm 6 and/or the main arm 7.

Each movement of the components of the stand may be summarized as a positioning of a corresponding kinematic axis of the x-ray imaging system 1, by which a positioning of the x-ray beam source 3 and the x-ray beam detector 2 may take place with respect to an object to be mapped, for instance with respect to the patient couch.

In accordance with the computer-implemented method for generating training data, target positioning data is predetermined for the imaging apparatus and in act S1 faulty positioning data 15 is calculated as a function of the target positioning data, the faulty positioning data deviating from the target positioning data by at least one predetermined positioning variance. To this end, variances in accordance with a statistical position distribution, for instance a Gaussian distribution, may be established for a corresponding axle clearance of one or more of the kinematic axes.

In act S2, an imaging method is simulated, in order to generate two or more simulated x-ray recordings 16, wherein a positioning of the imaging apparatus is simulated in accordance with the faulty positioning data 15.

In act S3, an annotated training data record 17 is generated and stored, which contains the two or more simulated x-ray recordings 16, and which contains at least one positioning variance as an annotation of the two or more simulated x-ray recordings 16.

Acts S1 to S3 may be repeated multiple times for instance, wherein with each repetition, the at least one positioning variance is determined again as a function of the statistical position distribution. A plurality of annotated training data records 17 may therefore be generated.

Furthermore, an initialized or pretrained algorithm 18 may be predetermined for estimating positioning variances in the imaging apparatus of an x-ray imaging system on the basis of x-ray recordings. The algorithm 18 contains in particular one or more artificial neural networks, for instance CNNs.

In act S4, the algorithm 18 is applied to the two or more simulated x-ray recordings 16, in order to predict at least one positioning variance.

In act S5, a predetermined cost function is evaluated on the basis of a difference in the at least one predicted positioning variance of at least one positioning variance, which contains the training data record 17 as an annotation, and the algorithm 18 is adjusted as a function thereof, in the case of a neural network for instance by back propagation. Acts S4 and S5 may likewise be repeated for different, or all training data records 17.

Figure 2:
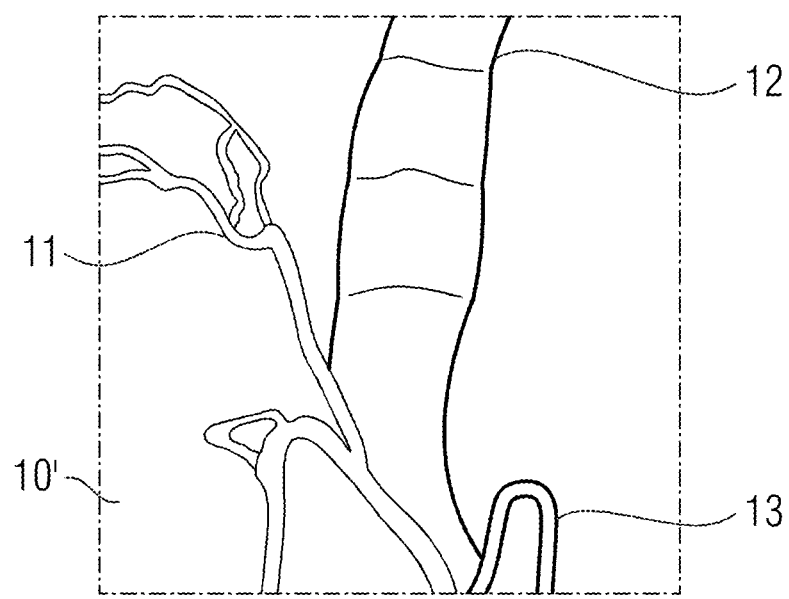
FIG. 2 depicts an example of a schematic representation of a subtraction angiography mapping with artifacts.

FIG. 2 shows a schematic representation of a subtraction angiography mapping 10' of a vascular tree 11, which was generated based on two x-ray recordings, wherein one of the x-ray recordings has been recorded with administering contrast agent and one of the x-ray recordings without administering contrast agent. As a result, the vascular tree 11 in the resulting subtraction angiography mapping 10' may be highlighted particularly clearly, wherein areas not influenced by the contrast agent are suppressed. In the subtraction angiography mapping 10', contours of a bone structure 12 and a catheter 13 may however be identified. This may revert back to positioning variances in the recording of the two x-ray recordings.

Figure 3:
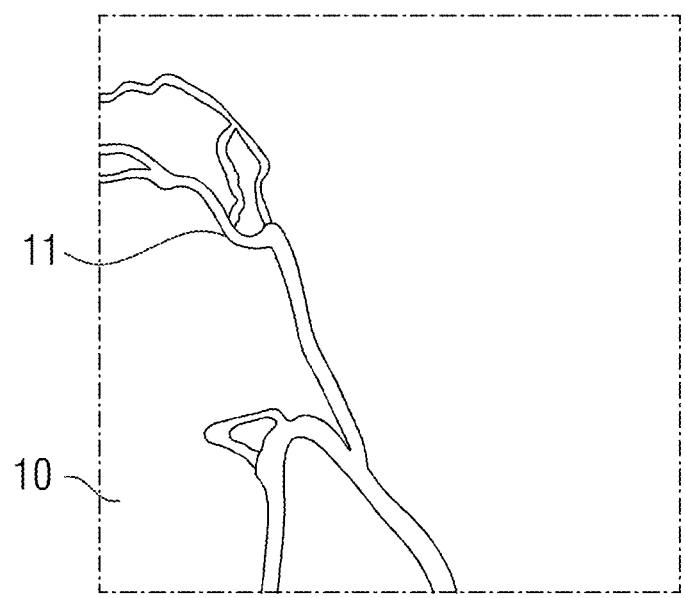
FIG. 3 depicts an example of a schematic representation of a further subtraction angiography mapping.

In order to prevent or reduce this, the trained algorithm 18 may be applied to two or more x-ray recordings, which have been recorded by the x-ray imaging system 1 in accordance with the predetermined target positioning data. An estimated positioning variance is determined as a result. The two or more x-ray recordings are corrected as a function of the estimated positioning variance and a further subtraction angiography mapping 10, as shown schematically in FIG. 3, is produced on the basis of the corrected x-ray recordings. The contours of the bone structure 12 and of the catheter 13 are suppressed therein.

In accordance with the disclosure, skeleton structures in the angiography and regions with a low resolution or unblurred regions may be identified in the x-ray recordings as interfering image artifacts and the x-ray recordings may be corrected accordingly.

In some embodiments, the causes of the positioning variances and/or their extent may be determined in order to correct the x-ray recordings in a targeted manner.

In order, in accordance with the disclosure, to generate training data, no true measurements have to be carried out on account of the simulation of the imaging method, so that the radiation load on patients and/or personnel may be reduced. In different embodiments, the simulation may include a combined simulation or co-simulation of mechanics and drive technology of the x-ray imaging system and the x-ray imaging.

Although the disclosure has been illustrated and described in detail by the exemplary embodiments, it is not limited by the disclosed examples and a person skilled in the art may derive other variations herefrom without departing from the scope of the disclosure.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A computer-implemented method for generating training data for training an algorithm for estimating positioning variances in an imaging apparatus of an x-ray imaging system, the computer-implemented method comprising:
predetermining target positioning data for the imaging apparatus;
calculating faulty positioning data as a function of the target positioning data, wherein the faulty positioning data deviates from the target positioning data by at least one predetermined positioning variance;
simulating an imaging method, wherein two or more simulated x-ray recordings are generated, wherein a positioning of the imaging apparatus is simulated in accordance with the faulty positioning data; and
generating and storing an annotated training data record that comprises the two or more simulated x-ray recordings and at least one positioning variance as an annotation of the two or more simulated x-ray recordings.

2. The computer-implemented method of claim 1, wherein the target positioning data establishes a target trajectory for the imaging apparatus and the faulty positioning data establishes a faulty trajectory for the imaging apparatus.

3. The computer-implemented method of claim 2, wherein the target trajectory for a target positioning of the imaging apparatus establishes a target time instant, and
wherein the faulty trajectory for the target positioning of the imaging apparatus establishes a faulty time instant that differs from the target time instant according to the at least one positioning variance.

4. The computer-implemented method of claim 2, wherein a first target positioning for a first simulated x-ray recording differs from a second target positioning for a second simulated x-ray recording in accordance with the target positioning data according to the target relative pose,
wherein a first faulty positioning for the first simulated x-ray recording deviates from a second faulty positioning for the second simulated x-ray recording in accordance with the faulty positioning data in accordance with a faulty relative pose, and
wherein the faulty relative pose deviates from the target relative pose.

5. The computer-implemented method of claim 4, wherein a third target positioning for a third simulated x-ray recording corresponds with a fourth target positioning for a fourth simulated x-ray recording in accordance with the target positioning data, and
wherein a third faulty positioning for the third simulated x-ray recording deviates from a fourth faulty positioning for the fourth simulated x-ray recording in accordance with the faulty positioning data.

6. The computer-implemented method of claim 1, wherein the at least one positioning variance is determined in accordance with a predetermined model for the positioning of the imaging apparatus.

7. The computer-implemented method of claim 6, wherein the positioning of the imaging apparatus is established by respective axis positions of kinematic axes of the x-ray imaging system,
wherein the predetermined model comprises a statistical position distribution according to a predetermined axle clearance at least for a first of the kinematic axes, and wherein the at least one positioning variance is determined as a function of the statistical position distribution.

8. The computer-implemented method of claim 7, wherein the calculating of the faulty positioning data, the simulating of the imaging method, and the generating and storing of the annotated training data record are repeated multiple times, and
wherein, with each repetition, the at least one positioning variance is determined again as a function of the statistical position distribution.

9. The computer-implemented method of claim 6, wherein the predetermined model comprises a reverberation characteristic, and
wherein the at least one positioning variance is determined at least in part in accordance with the reverberation characteristic.

10. The computer-implemented method of claim 1, wherein target dose data is predetermined,
wherein faulty dose data is calculated as a function of the target dose data,
wherein the faulty dose data deviates from the target dose data by at least one dose variance,
wherein, when the imaging method is simulated, an emission of x-ray radiation is simulated in accordance with the faulty dose data, and
wherein the annotated training data record comprises the at least one dose variance as a further annotation of the two or more simulated x-ray recordings.

11. The computer-implemented method of claim 1, further comprising:
predicting at least one positioning variance by applying the algorithm to the two or more simulated x-ray recordings; and
adjusting the algorithm as a function of the at least one predicted positioning variance and the at least one positioning variance of the annotated training data record.

12. A method for x-ray imaging, the method comprising:
generating two or more x-ray recordings of an object to be mapped by an x-ray imaging system;
positioning an imaging apparatus of the x-ray imaging system in accordance with predetermined target positioning data;
estimating at least one positioning variance by applying an algorithm trained in accordance with a computer-implemented method to the two or more x-ray recordings; and
correcting the two or more x-ray recordings as a function of the at least one estimated positioning variance.

13. The method of claim 12, wherein a three-dimensional reconstruction of the object to be mapped is generated based on the corrected two or more x-ray recordings.

14. The method of claim 13, wherein at least one subtraction angiography mapping of the object to be mapped is additionally generated based on the corrected two or more x-ray recordings.

15. The method of claim 12, wherein at least one subtraction angiography mapping of the object to be mapped is generated based on the corrected two or more x-ray recordings.

16. A data processing apparatus comprising:
at least one processing switching circuit,
wherein the data processing apparatus is configured to adjust the at least one processing switching circuit by:
predetermining target positioning data for an imaging apparatus;
calculating faulty positioning data as a function of the target positioning, wherein the faulty positioning data deviates from the target positioning data by at least one predetermined positioning variance;
simulating an imaging method, wherein two or more simulated x-ray recordings are generated, wherein a positioning of the imaging apparatus is simulated in accordance with the faulty positioning data;
generating an annotated training data record that comprises the two or more simulated x-ray recordings and at least one positioning variance as an annotation of the two or more simulated x-ray recordings;
predicting at least one positioning variance by applying an algorithm to the two or more simulated x-ray recordings; and
adjusting the at least one processing switching circuit as a function of the at least one predicted positioning variance and the at least one positioning variance of the annotated training data record.

* * * * *